(12) United States Patent
Batchelor et al.

(10) Patent No.: US 12,324,616 B2
(45) Date of Patent: Jun. 10, 2025

(54) TISSUE THERAPY ENERGY DELIVERY USING OPTICAL IMAGING

(71) Applicants: GYRUS ACMI, INC., Westborough, MA (US); Teo Heng Jimmy Yang, Heath Cardiff (GB)

(72) Inventors: Kester Julian Batchelor, Mound, MN (US); Teo Heng Jimmy Yang, Heath (GB); Takeshi Onaga, Medina, MN (US); Jordan R. Golomb, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/548,764

(22) PCT Filed: Mar. 2, 2022

(86) PCT No.: PCT/US2022/070924
§ 371 (c)(1),
(2) Date: Sep. 1, 2023

(87) PCT Pub. No.: WO2022/187832
PCT Pub. Date: Sep. 9, 2022

(65) Prior Publication Data
US 2024/0099763 A1 Mar. 28, 2024

Related U.S. Application Data

(60) Provisional application No. 63/265,978, filed on Dec. 23, 2021, provisional application No. 63/271,053, (Continued)

(51) Int. Cl.
*A61B 18/14* (2006.01)
*A61B 90/00* (2016.01)
*A61B 18/00* (2006.01)

(52) U.S. Cl.
CPC ........ *A61B 18/1442* (2013.01); *A61B 90/361* (2016.02); *A61B 2018/00184* (2013.01); (Continued)

(58) Field of Classification Search
CPC ...... A61B 18/1442; A61B 2018/00184; A61B 2018/00648; A61B 2018/00702; A61B 2018/00875; A61B 2018/00964
See application file for complete search history.

(56) References Cited

U.S. PATENT DOCUMENTS

2015/0320433 A1* 11/2015 Navve ................. A61B 17/225
606/2.5
2017/0143260 A1* 5/2017 Latimer ................ A61B 18/20
(Continued)

FOREIGN PATENT DOCUMENTS

CN 117460474 A 1/2024
DE 112022001331 T5 12/2023
(Continued)

OTHER PUBLICATIONS

"International Application Serial No. PCT/US2022/070924, International Search Report mailed Aug. 26, 2022", 9 pgs.
(Continued)

*Primary Examiner* — Michael F Peffley
*Assistant Examiner* — Samantha M Good
(74) *Attorney, Agent, or Firm* — Schwegman Lundberg & Woessner, P.A.

(57) ABSTRACT

A system for imaging and treating tissue can include or use an imaging sensor adapted to receive imaging information from a location internal to a human or animal subject, a tissue therapy output for applying a tissue therapy to tissue at the location internal to the subject, and controller circuitry, comprising signal-processing circuitry configured for image-processing the imaging information to determine a
(Continued)

structure or other characteristic at or near the location internal to the subject, and to tailor a parameter or algorithm, controlling the tissue therapy output, at least in part based on the imaging information.

20 Claims, 6 Drawing Sheets

Related U.S. Application Data filed on Oct. 22, 2021, provisional application No. 63/155,444, filed on Mar. 2, 2021.

(52) U.S. Cl.
CPC .............. *A61B 2018/00648* (2013.01); *A61B 2018/00702* (2013.01); *A61B 2018/00875* (2013.01); *A61B 2018/00964* (2013.01)

(56) References Cited

U.S. PATENT DOCUMENTS

| 2018/0235484 | A1* | 8/2018 | Mozdzierz | ............ | A61B 17/29 |
| 2019/0223946 | A1* | 7/2019 | Coates | ................ | A61N 1/0551 |
| 2020/0015899 | A1 | 1/2020 | Scheib et al. | | |
| 2020/0211181 | A1 | 7/2020 | Govari et al. | | |
| 2020/0237237 | A1 | 7/2020 | Mozdzierz | | |
| 2020/0246033 | A1* | 8/2020 | Burkhard | ............. | A61B 90/361 |
| 2021/0177488 | A1* | 6/2021 | Allen, IV | ........... | A61B 18/1445 |

FOREIGN PATENT DOCUMENTS

| EP | 3669796 A1 | 6/2020 |
| WO | WO-2022186959 A1 | 9/2022 |
| WO | WO-2022187832 A2 | 9/2022 |
| WO | WO-2022187832 A3 | 9/2022 |

OTHER PUBLICATIONS

"International Application Serial No. PCT/US2022/070924, Written Opinion mailed Aug. 26, 2022", 14 pgs.

"Chinese Application Serial No. 202280026537.8, Notification to Make Rectification mailed Nov. 1, 2023", W/O English Translation, 1 page.

"Chinese Application Serial No. 202280026537.8, Response filed Dec. 18, 2023 to Notification to Make Rectification mailed Nov. 1, 2023", w/o English Translation, 3 pgs.

"European Application Serial No. 22715498.6, Voluntary Amendment Filed Dec. 8, 2023", 16 pgs.

"International Application Serial No. PCT/US2022/070924, International Preliminary Report on Patentability mailed Sep. 14, 2023", 16 pgs.

* cited by examiner

TISSUE THERAPY ENERGY DELIVERY USING OPTICAL IMAGING

CLAIM OF PRIORITY

This application is a U.S. national stage filing under 35 U.S.C. § 371 from International Application No. PCT/US2022/070924, filed on Mar. 2, 2022, and published as WO2022/187832 on Sep. 9, 2022, which claims the benefit of priority to each of US Provisional Applications Ser. No. 63/155,444, filed on Mar. 2, 2021, Ser. No. 63/271,053, filed on Oct. 22, 2021, and Ser. No. 63/265,978, filed on Dec. 23, 2021, each of which are incorporated by reference herein in their entireties, and the benefit of priority of each of which is claimed herein.

BACKGROUND

Various different types of energy, e.g., radio frequency (RF) or other electromagnetic energy, plasma energy, or ultrasound energy can be used for vessel sealing, tissue cutting or cautery, tissue ablation, or tissue coagulation, among other things, alone or in combination with mechanical energy delivery (e.g., using a sharp cutting instrument) or manipulation (e.g., using a forceps). Many types of monopolar and bipolar energy devices exist for different surgical purposes. In one example of an energy delivery device ("energy device"), a forceps can be utilized such as for laparoscopic surgery. The forceps can be employed such as to control delicate movements inside a patient and can include a gripping assembly and/or a cutting assembly. Further, the forceps can utilize electrical energy in the gripping assembly. Electrosurgical sealing forceps can further include or use an energy device such as RF, ultrasonic, and microwave vessel sealing devices. The forceps can clamp tissue, and elastin or collagen of the clamped tissue can be melted by the energy device such as can seal the tissue.

SUMMARY

The present inventors have recognized, among other things, that tissue treatment procedures using energy delivery can benefit from improvements including reduced procedure time, reduced complications from treatment, and reducing the requisite skill level of the surgeon or other practitioner performing the procedure, such as to help reduce or avoid the need for surgical "tricks" or techniques to accommodate changing conditions at a target site during the procedure. For example, an approach to electrosurgery may include or use an electrosurgical device with an radio frequency (RF) or other electromagnetic energy delivery system with nearly instantaneous feedback about one or more conditions (e.g., tissue impedance, phase angle of therapy power delivery, or the like) at the target site to adjust electrosurgical therapy energy delivered to the tissue at the target site based on an electrical feedback signal representative of one or more such conditions at the target site. However, a single, common RF electromagnetic energy waveform application process might be applied to different tissue types-such as which can exhibit different characteristics during a particular procedure, such as during vessel sealing, or during monopolar or bipolar cutting or any other tissue treatment. For example, a carotid artery and a renal artery have different vessel sealing characteristics but, in one approach, each of such vessels would likely be controlled by the same therapy energy waveform application process. Similar considerations can exist for other tissues, such as which can potentially be treated more specifically, for example, such as fats, or ligaments, or other tissues. Thus, in some cases, the electrical tissue characteristic (e.g., tissue impedance) feedback from the target tissue site alone may not be enough to appropriately adjust energy therapy delivery, or may not be enough to appropriately distinguish between tissue types to allow tailoring or adjustment or other nuances in the way that the electrical energy is delivered to the target tissue site. For example, the present inventors have recognized, among other things, that a carotid artery should have electrical therapy power applied relatively more slowly, e.g., for vessel sealing, while a renal artery can tolerate faster power application without creating tissue "popping" problems. Such tissue popping is a phenomena in which steam generated within the tissue exits, e.g., from between forceps jaws, applying mechanical pressure and electrical energy together, at such speed that it can cause damage to the vessel wall including at one or more locations that can be away from the target vessel sealing site. Thus, feedback, in addition to or other than electrical feedback, can be used to help make different, e.g., better tailored, energy delivery decisions.

An approach to electrosurgery can also help administer a target closure force supplied by an end effector, regardless of the amount of tissue along the contact area of the jaws. For example, an electrosurgical system can help a user achieve a desired tissue pressure between the jaws during electrosurgical treatment. The target closure force can be determined by the system based on visualization feedback. In an example, the system can determine the target tissue pressure based upon a vessel type, and subsequently determine the target closure force required to supply the target tissue pressure to the vessel. In another example, the target tissue pressure can be estimated based upon a measured tissue parameter such as a vessel diameter and the system can subsequently determine the target closure force required to supply the target tissue pressure to the tissue. The system can include or use a processing unit configured to establish, adjust, or modulate a jaw closure force or an energy waveform based on data collected from the sensor. The processing unit can use data collected from the sensor such as to help determine the target tissue pressure or the target closure force.

DETAILED DESCRIPTION

Figure 1A:
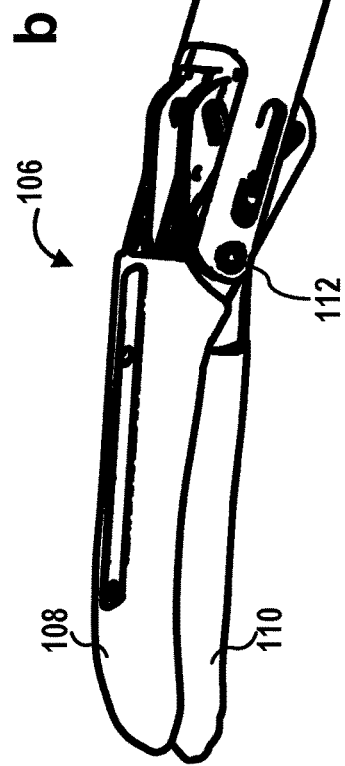
FIG. 1A illustrates a side view an example of an electrosurgical system.

This disclosure relates to devices and methods for treating tissue such as, but not limited to, blood vessels. In an approach to tissue treatment an energy device, such as radio frequency (RF), ultrasonic, and microwave vessel sealing devices, can be used as a part of an electrosurgical sealing forceps. An end effector assembly, such as can include a forceps, can provide a desired jaw pressure such to compress the tissue for electrosurgical sealing. The energy devices can be used such as to apply energy to treat one or more tissue components, e.g., collagen or elastin of the tissue, and the heated or melted components can be used such as to seal to the tissue. Certain electrosurgical sealing forceps can also include a cutting element as part of the end effector, such as a stationary or moveable cutting blade to cut the sealed vessel. Such devices can use a relatively high jaw closure force to compress the vessel tissue for sealing. A problem with this approach, however, that an undesired jaw closure force can cause unwanted tissue damage during the procedure if the tissue is not held at an appropriate target tissue pressure. Providing the appropriate target tissue pressure can be challenging for users, for example, if the region between the jaws is not filled with tissue. In such a case, the closure force needed from the end effector to supply the target tissue pressure can vary based on the amount of tissue is in contact with a contact surface area of the jaws. For instance, at a fixed closure force in a case in which the jaws compress a relatively small amount of tissue, a greater tissue pressure is supplied than in a case in which the jaws compress a relatively large amount of tissue at the same fixed closure force. Also, providing the desired tissue pressure can be challenging for users due to varying tissue thickness, morphology, size, volume, density, composition, moisture content, and the like. Generally, the "target tissue pressure" can refer to relatively small range of acceptable pressures for the procedure and supplying the target tissue pressure can be significant such as for a user to perform a successful procedure. If too little closure force is applied, the tissue is compressed at too small of a tissue and the resultant seals created can be very low in their 'burst pressure' (e.g., the blood pressure required to prevent the created seal from breaking). This is because the 'glue' created from the melted elements of the vessels such as the collagen, is not squeezed together sufficiently. This insufficient pressurization of the glue can result in a weakness at the pressure-treated joint interface and results in poor seals. If too great of closure force is applied, the tissue pressure is too great and, irrevocable tissue damage can occur such as tearing and ripping of the tissue. Also, if too great of closure force is applied, the tissue pressure is too great and, tissue popping can occur when the steam generated within the tissue while applying energy is trapped between the jaws at the high pressure until the jaws are released following the procedure. At this point, the steam within the walls of the vessel can escape at a high velocity and can damage surrounding tissue. This can result in behind-the-seal weaknesses that can later burst during times of patient recovery from anesthesia or post-operatively (due to the increase of a patient's blood pressure meeting the particular blood pressure level within the vessel that causes failure at the weakened location of the "sealed" blood vessel).

The present inventors have recognized, among other things, that creating a tissue treatment system that can determine and provide a 'target' closure force supplied by an end effector, regardless of the amount of tissue along the contact area of the jaws, can help a user achieve the target tissue pressure between the jaws during energy delivery treatment, such as for vessel sealing. The target closure force can be determined and established or adjusted by the system, such as based on visualization feedback such as using a tissue image generated by an imaging sensor such as a camera. In an example, the system can use information from the image to help determine the target tissue pressure based upon, e.g., an identified tissue type, such as a vessel type, and subsequently determine the target closure force appropriate to supply the target tissue pressure to the blood vessel or other tissue. In another example, the target tissue pressure can be estimated or calculated based upon one or more measured tissue parameters, such as, but not limited to, a cross-sectional vessel dimension such as a vessel diameter and the system can subsequently determine the target closure force required to supply the target tissue pressure to the tissue. Since vessels are natural and they do not conform to exact circles in cross-section, the vessel diameter can include an approximated diameter, measured diameter, average diameter, minimum diameter, maximum diameter, or calculated diameter obtained from one or more measurements. The one or more tissue parameters can additionally or alternatively correspond to one or more of a thickness, morphology, size, volume, density, composition, moisture content, dynamic modulus, viscoelastic properties, conductivity, impedance, color, or non-visible light reflection, scattering, or other optical response feedback, or other delineable property of the tissue. Alternatively or additionally, the system can use the tissue parameter(s) to establish, adjust, or modulate another parameter of the electrosurgical system such the amplitude, frequency, pulse width, current, phase angle, or other electrical property of an electrosurgical energy signal. The system can include or use a processing unit configured to establish, adjust, limit, or modulate one or both of a jaw closure force or an energy waveform, such as can be based on data collected from the imaging and/or other sensor. The processing unit 122 can use data collected from the sensor such as to determine the target tissue pressure or the target closure force. Tailoring one or both of the force or electrical properties applied by the device to the one or more tissue parameters can be beneficial because it can provide improved performance of the device across different tissues.

Specific tissues or tissue types, e.g., within an area of visualization, can be identified, such as using one or more visualization or optical imaging techniques. Such techniques can include using image signal processing, such as together with a trained learning model, e.g., trained using one or more machine learning or other artificial intelligence (AI) techniques, such as to help identify one or more specific tissues, tissue types, or tissue structures, or the like, at or near a target site or scene, such as within an endoscopic, laparoscopic, or other patient-internal area of visualization. Specific tissues can be also identified at patient-external areas of visualization. For example, this sort of visualization or optical imaging can be configured to use visualization or optical imaging information to identify specific anatomy or tissue, or a characteristic thereof. When the tissue is positioned or located, such as with respect to the end effector, for vessel sealing or similar therapy, such as by an electrotherapy or other therapeutic medical device, a particular therapy or therapy parameter setting (e.g., process, waveform, or the like) can be selected. The particular therapy or therapy parameter setting can be selected from multiple available therapies or therapy parameter settings, such as can be tailored based at least in part using the visualization or optical imaging information. As explained herein, the visualization or optical imaging information can also be used in combination with other information, such as electrical information (e.g., tissue impedance). In an example, when the tissue type or characteristic cannot be determined (e.g., to a desired degree of accuracy) using the visualization or optical imaging technique, a particular "compromise" vessel sealing (or other therapy) therapy or therapy waveform or parameter can be selected, such as based at least in part upon suitability for all or a variety or subset of tissue types, or based at least in part on an electrical tissue characteristic, such as a tissue impedance characteristic, a phase angle of therapy power delivery, or the like.

FIG. 1A, FIG. 1B, FIG. 1C, FIG. 1D, and FIG. 1E illustrate an example of portions of an electrosurgical system 100. The electrosurgical system 100 can include or use a medical device 102 having an end effector assembly 104. As described herein, the system 100 can be configured to deliver a tailored energy output to a variety of devices. In the illustrative example, the system 100 can provide tailored waveforms to one or more electrodes, such as an active electrode 111 (electrode 111 depicted in FIG. 1D). Such tailored energy output can be used to treat the tissue, such as to seal, cut, ablate, fulgurate or desiccate, among other effects. In some examples, the end effector assembly 104 includes both an active electrode and a return electrode, however, the device does not have to be a forceps or be bipolar as shown in the illustrative example. Waveforms delivered by the processing unit 122 can be tailored for monopolar and other types of devices as well. For example, an active electrode of a device can be used in conjunction with a remote return electrode, such as, but not limited to a return electrode pad.

Furthermore, the tailored energy outputs described herein can be used in systems that deliver any type of energy output that is compatible with a particular end effector or device. In merely a few non-limiting examples provided for the sake of clarity, tailoring an energy output can include tailoring the ultrasonic energy or radiofrequency energy delivered by to/by an ultrasonic forceps, or tailoring the thermal energy delivered to/by forceps or other device for treatments such as cutting, sealing, coagulation, ablation, desiccation, fulguration, and the like.

The end effector assembly 104 can include or use a jaw assembly 106. Alternatively or additionally, the end effector assembly 104 can include or use a "J-shaped Hook" type electrode or other electrode types for surgery. The jaw assembly 106 can include a first jaw member 108 and a second jaw member 110. The second jaw member 110 can be pivotably coupled to the first jaw member 108 about a pivot axis or other pivot point 112. One or more drives 119 can be included or used in the device 102, such as housed within the handle 118 and mechanically coupled to the end effector assembly 104. Also, one or more drives 119 can be included at or near the distal end of the assembly 104 such directly driving the jaw assembly 106. The drive 119 can be any suitable drive associated or coupled with the end effector in any arrangement, including, e.g., robotic applications.

The electrosurgical system 100 can also include or use one or more onboard or separate sensors 114 for determining a tissue characteristic. For example, as depicted in FIG. 1A, the sensor 114 can be separate from the end effector assembly, such as extending from another shaft or mount of the device 102, or such as extending from another device such as a robotic arm or videoscope. Also, the sensor 114 can be integrated at or near the end effector assembly 104. Types of force sensors can include, for example, strain, piezoelectric, inductive, capacitive, magnetostrictive, hydraulic or pneumatic, that can measure forces such as compression, strain, contact, displacement, bending, tension, shear or torque. Such a force sensor 114 (or electrical sensor 114) can be located in the end effector 104, for example, a component of one or more of the jaw members 108, 110, or the tissue sealing plates 109, which in this example can include active electrode 111 and return electrode 113. The force sensor 114 can be located in any other suitable location on the forceps for measuring force or displacement of the jaws 108, 110. In an example, the sensor 114, such as a camera, can be located at or near the distal end of the end effector assembly, on a jaw of the jaw assembly 106, or integrated with a end effector assembly 104, such as a J-hook (as depicted in FIG. 1E).

Figure 1B:
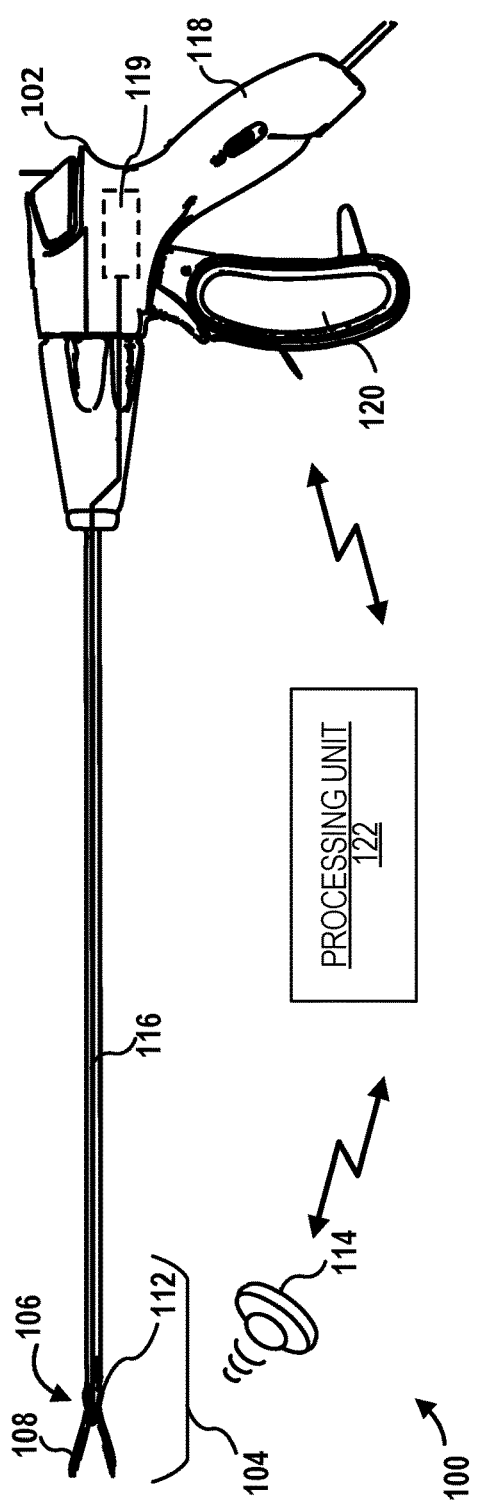
FIG. 1B illustrates an example of a jaw assembly in a first position.
Figure 1C:
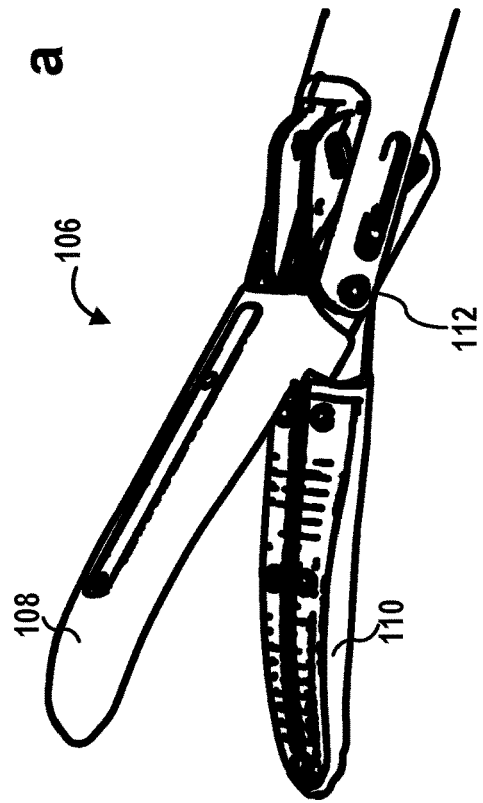
FIG. 1C illustrates an example of a jaw assembly in a second position.
Figure 1E:
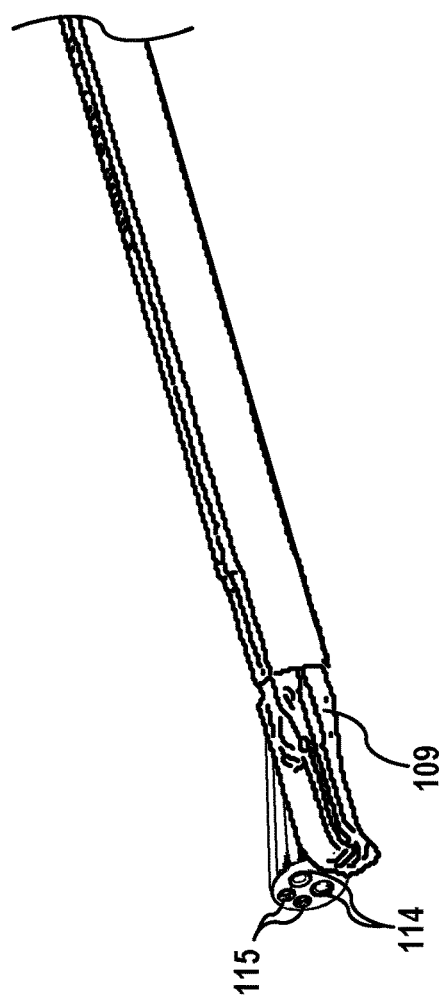
FIG. 1E illustrates an example of an integrated camera for use with an end effector assembly.
Figure 1D:
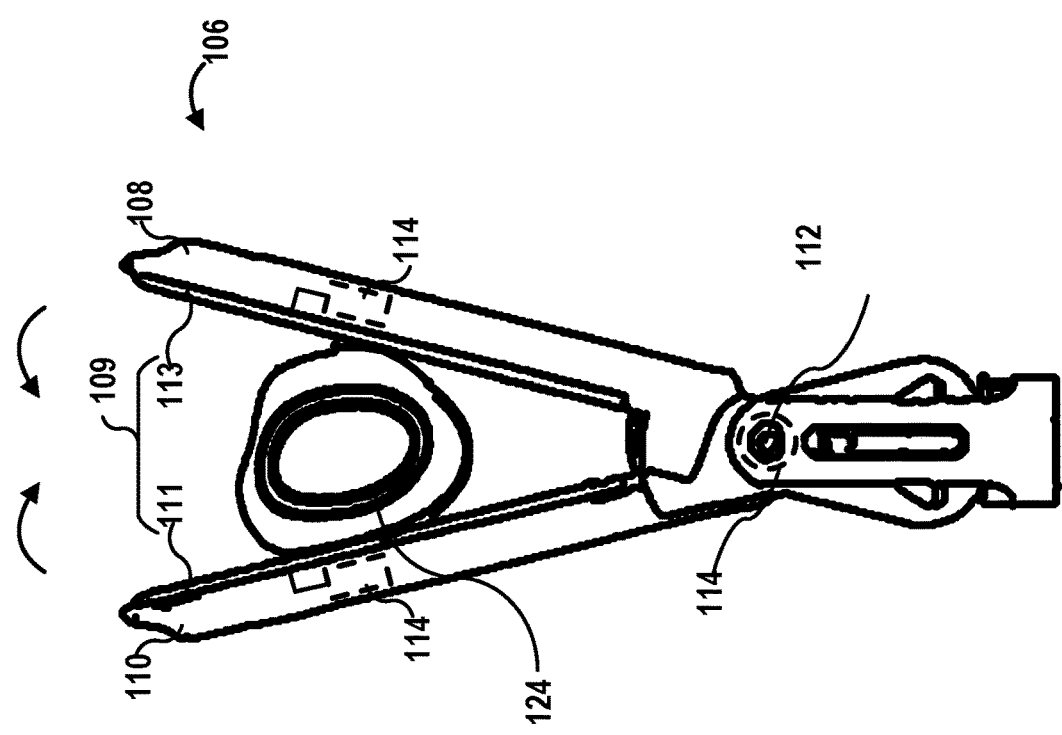
FIG. 1D illustrates an example of an electrosurgical system compressing a target object.

As shown in FIG. 1B and FIG. 1C, the jaws 108 and 110 of the jaw assembly 106 can be movable between a first position a, in which the first and second jaw members 108 and 110 are spaced apart from each other and a second position b, in which the first and second jaw members 108 and 110 are positioned closer to each other than in the first position a. As depicted in FIG. 1D, the end effector assembly 104 can compress a blood vessel or other target object 124, such as a part of a body, an anatomical feature, tissue, veins, arteries, or a combination thereof of a human or animal subject. In an example, the end effector assembly 104 can be used in the system 100 such as to compress one or more of lymphatics, tissue pedicles, arteries, and veins, such as with a diameter or similar cross-sectional dimension ranging from about 0.5 mm to about 7 mm. Herein, a diameter of a vessel can refer to either of a measured diameter or an average diameter along a length of interest of a vessel of interest. In another example, end effector assembly 104 can be used in the system 100 such as to compress lymphatics or arteries with a diameter or other similar cross-sectional dimension greater than 7 mm. At least one of the first and second jaw members 108 and 110 can include electrodes that can be adapted such as to be electrically connected to an electrosurgical energy source, such as to provide current that can be passed through the electrodes of the end effector assembly 104. For example, a therapy current can be passed from the first jaw member 108 to the second jaw member 110 when tissue is located within the jaw and the therapy current can coagulate blood, cauterize, cut, or a combination thereof. The end effector assembly 104 can generally include one or more working assemblies, such as pairs of jaws, and sufficient controls to work the one or more working assemblies. The end effector assembly 104 can include parts employed to perform the recited functions and can include an elongated or other shaft 116 (e.g., a tubular member, a hollow tube, or an assembly of tubes), a hand piece 118, one or more operable mechanisms used to manipulate the shaft 116 or to actuate the end effector assembly 104, such as an actuator 120, or a combination thereof. The hand piece 118 can be an assembly of parts or housing structures capable of forming a hand piece 118 structure with a cavity. In an example, the shaft 116 and the end effector assembly 104 can be included with or mounted to the end of a robotic arm such as to permit robotic stabilization, positioning, manipulation, and operation, instead of being hand-held by a user grasping the hand piece 118.

In an example, the sensor 114 can include a camera capable of illuminating and capturing a tissue image, such as using a focal plane array (FPA) imaging sensor array of pixels. For example, as depicted in FIG. 1E, the sensor 114 can be a camera located at the distal end of the end effector assembly 104. One or more cameras 114 can be integrated at or near a jaw assembly 106 or a J-hook (as shown). One or more light sources 115 can be included in the system 100, such as near the camera 114, such as for illumination of the surgical site. Where, the camera 114 is integrated into the device 102, manipulation of the device can simultaneously or concurrently position both the camera 114 and the tissue image can include one or more device-recognizable features of the tissue, such as by applying a trained learning model or other image signal processing to the image to recognize one or more features in the image. The sensor 114 can also include an electrical sensor or electrode, such as for providing electrical characterization of tissue compressed between the first jaw member 108 and the second jaw member 110, either during or after or interleaved with application of electrosurgical treatment energy to the tissue. Also, the sensor 114 can be accompanied by an optical fiber bundle or other illumination optics such as to communicate light from an external light source to an internal target, and can include one or more of a spectroscopic imaging or analysis sensor, a hyperspectral imaging sensor, a colorimetric imaging sensor, a video camera sensor, an infrared imaging sensor, an ultrasound imaging sensor, a 3D imaging sensor, a LIDAR imaging sensor, an optical coherence tomography (OCT) imaging sensor, a focal plane array (FPA) imaging sensor, or a fluorescence or other shifted-wavelength response imaging sensor. The sensor 114 can include a force sensor such as embedded or otherwise included in the jaw assembly 106 to measure a displacement of clamping force by the tissue. The force sensor included in the sensor 114 can include, e.g., a strain gauge, a load cell, a piezoresistive sensor, an inductive sensor, a capacitive sensor, or a magnetostrictive sensor. The sensor 114 can include an electrical sensor for measuring one or more electrical properties such as electrical properties of tissue, e.g., resistance, capacitance, or inductance.

The sensor 114 can be communicatively coupled to a processing unit 122. The processing unit 122 can receive data from the sensor 114 and, based thereon, can determine a compression force parameter such as a target clamping force of the jaw assembly 106 using the data. In an example, the processing unit 122 can generate a tissue image of the tissue compressed between the first jaw member 108 and the second jaw member 110. The tissue image can include one or more device-recognizable features of the tissue. The processing unit 122 can be configured such as to recognize or identify various types or properties of tissue or vessels such as a carotid artery, a femoral artery, a renal artery, a pulmonary artery, or other types of specific arteries, veins, or lymphatics. In an example, the processing unit 122 can use a trained learning model, an algorithmic signal processing approach, or both, such as to recognize or identify one or more device-recognizable features of the tissue image such as one or more shapes, patterns, colors. These features can be cross-referenced to a database of image feature data, in an example. The processing unit 122 can further manipulate the image, the features, or both, such as changing from color to greyscale or monochrome or segmenting or outlining of certain features, such as to help improve feature recognition. In an example, depth-of-field analysis circuitry can be included or used by the processing unit 122 such as to help obtain representations of 3D features of the tissue.

Also, the processing unit 122 can include or use or be capable of executing a machine learning model trained to recognize or identify various types of vessels using the specimen image. The processing unit 122 can include or use one or more algorithms capable of extracting data from the specimen image, such as data by compression, filtering, edge detection, corner detection, blob detection, ridge detection, Hough transform, image segmentation, optical flow, genetic algorithms (GA), or other techniques for algorithmically analyzing the specimen image. The one or more algorithms can be capable of digital image processing such as to extract relevant data from the specimen image to enable recognition of relevant vessel features. The machine learning model can include or use training data received as an input, such as training data classified from a human user. The model can include or use one or more predictive engines. The predictive engine can include or use several engine parameters such as data sources, algorithms, configuration inputs, or other characteristics of the engine under consideration. The predictive engine can include a data source parameter such as for user-input symptom data. The model can include a plurality of algorithms and source code to generate a predictive engine variant by using the training data to help algorithmically arrive upon a label representing the correct identification of a vessel. The model can replace the predictive engine variant with a new predictive engine variant based on the training data received as an input, performance of the predictive engine variant, or both. The predictive engine variant can be chosen by an operator such as the human user or can be generated automatically. Selections of the engine parameters can be tagged or replayed by the predictive engine such as to evaluate and tune the predictive engine. In some examples, the operator can determine one or more new engine variants manually such as to troubleshoot, tune, or otherwise override the predictive engine. The predictive engine can include or use training data locally, such as to receive training data exclusively with respect to a plurality of specimen images generated by a single user. Alternatively or additionally, the predictive engine can include or use training data globally, such as to receive training data collectively with respect to specimen images generated by a plurality of users. The predictive engine can interact with one or more servers which can be capable of data storage, local data communication, global data communication, or any combination thereof. The predictive engine can interact with a website such as for global data communication.

The machine learning model can be an artificial neural network in some implementations. Artificial neural networks are artificial in the sense that they are computational entities, inspired by biological neural networks but modified for implementation by computing devices. Artificial neural networks are used to model complex relationships between inputs and outputs or to find patterns in data, where the dependency between the inputs and the outputs cannot be easily ascertained. A neural network typically includes an input layer, one or more intermediate ("hidden") layers, and an output layer, with each layer including a number of nodes. The number of nodes can vary between layers. A neural network is considered "deep" when it includes two or more hidden layers. The nodes in each layer connect to some or all nodes in the subsequent layer and the weights of these connections are typically learnt from data during the training process, for example through backpropagation in which the network parameters are tuned to produce expected outputs given corresponding inputs in labeled training data. Thus, an artificial neural network is an adaptive system 100 that is configured to change its structure (e.g., the connection configuration and/or weights) based on information that flows through the network during training, and the weights of the hidden layers can be considered as an encoding of meaningful patterns in the data.

A fully connected neural network is one in which each node in the input layer is connected to each node in the subsequent layer (the first hidden layer), each node in that first hidden layer is connected in turn to each node in the subsequent hidden layer, and so on until each node in the final hidden layer is connected to each node in the output layer.

In an example, the machine learning model can include or use a Convolutional Neural Network (CNN). A CNN is a type of artificial neural network, and like the artificial neural network described above, a CNN is made up of nodes and has learnable weights. However, the layers of a CNN can have nodes arranged in three dimensions: width, height, and depth, corresponding to the 2×2 array of pixel values in each video frame (e.g., the width and height) and to the number of video frames in the sequence (e.g., the depth). The nodes of a layer may only be locally connected to a small region of the width and height layer before it, called a receptive field. The hidden layer weights can take the form of a convolutional filter applied to the receptive field. In some examples, the convolutional filters can be two-dimensional, and thus, convolutions with the same filter can be repeated for each frame (or convolved transformation of an image) in the input volume or for designated subset of the frames. In other examples, the convolutional filters can be three-dimensional and thus extend through the full depth of nodes of the input volume. The nodes in each convolutional layer of a CNN can share weights such that the convolutional filter of a given layer is replicated across the entire width and height of the input volume (e.g., across an entire frame), reducing the overall number of trainable weights and increasing applicability of the CNN to data sets outside of the training data. Values of a layer may be pooled to reduce the number of computations in a subsequent layer (e.g., values representing certain pixels may be passed forward while others are discarded), and further along the depth of the CNN pool masks may reintroduce any discarded values to return the number of data points to the previous size. A number of layers, optionally with some being fully connected, can be stacked to form the CNN architecture. The machine learning model can also be at least one of Support Vector Machine (SVM), K-Nearest Neighbors (KNN), Artificial Neural Network (ANN), or an ensemble model combining the SVM and ANN.

In an example, the processing unit 122 can use the data from the sensor 114 to measure or estimate a diameter of a vessel sensed by the sensor, such as a vessel in view of or in contact with the sensor, a vessel located between the first jaw member 108 and second jaw member 110, or a vessel compressed between the first jaw member 108 and the second jaw member 110. For example, device-recognizable features from the specimen image can be used by the processing unit 122 such as to measure or estimate the diameter of the vessel. Also, a pivot angle of the first jaw member 108 and the second jaw member 110 can be measured and used such as to help estimate the diameter of the vessel. Also, the processing unit 122 can use the data from the sensor 114 to measure or estimate the amount of tissue compressed between the jaws. The processing unit 122 can use the data from the sensor 114 to determine a contact area of the tissue compressed between the first jaw member 108 or the second jaw member 110. As described herein, the vessel diameter or other cross-sectional outer or inner dimension can include an approximated diameter, measured diameter, average diameter, minimum diameter, maximum diameter, or calculated diameter obtained from one or more measurements.

The processing unit 122 can determine the target tissue pressure based upon, e.g., an identified vessel type, an identified vessel location, or an identified vessel diameter. The processing unit 122 can determine the target closure force based upon, e.g., the amount of tissue sensed by the sensor, located between the jaws, compressed between the jaws, the contact area of the tissue compressed between the jaws, an identified vessel type, and identified vessel location, or an identified vessel diameter. The processing unit 122 can help deliver the determined target closure force based to the end effector assembly 104. The end effector can receive an input from the processing unit 122 such as to apply the target closure force by actuation of one or more drives, e.g., motors, micromotors, etc. In another example, a robotics unit can receive an input from the processing unit 122 such as to apply the target closure force. In an example, the target closure force or the target tissue pressure can be determined by the processing unit 122 and can function as threshold inputs for user feedback. For instance, a user of the end effector assembly 104 can receive visual or audible or haptic or other feedback from the processing unit 122 upon meeting or exceeding the determined target closure force or the determined target tissue pressure. Also, the user can receive visual or audible or haptic or other feedback when nearing the determined target closure force or the determined target tissue pressure.

In another example, the processing unit 122 can determine the target tissue pressure or target closure force and use either of the two to establish, adjust, or modulate the energy waveform such as to help compensate for, e.g., too great of tissue pressure or closure force. Alternative or additional to adjusting a target clamping force, a magnitude of the electrosurgical energy can be established or adjusted such as to mitigate potential side-effects of therapy to a patient, such as tissue overcooking or "popping". For example, an electrosurgical system 100 can be configured to use visualization or optical imaging information to identify specific anatomy or tissue, or a characteristic thereof. When the tissue is positioned or located for vessel sealing or similar therapy, such as by an electrotherapy or other therapeutic medical device, a particular therapy or therapy parameter setting (e.g., process, waveform, or the like) can be selected, such as from multiple available therapies or therapy parameter settings, such as can be tailored based at least in part using the visualization or optical imaging information, which can also be used in combination with other information, such as electrical information (e.g., tissue impedance). In an example, when the tissue type or characteristic cannot be determined (e.g., to a desired degree of accuracy) using the visualization or optical imaging technique, a particular "compromise" vessel sealing (or other therapy) therapy or therapy waveform or parameter can be selected, such as based at least in part upon suitability for all or a variety of tissue types, or based at least in part on an electrical tissue characteristic, such as a tissue impedance characteristic, a phase angle of therapy power delivery, or the like. In the case where the tissue type or characteristic cannot be determined sufficiently by the processing unit 122, an alert can be output to notify the user of such event; to inform the user that a less-tailored output is being provided; or to alert the user to reposition the end-effector with respect to the tissue such as for undertaking additional sensing.

The feedback or other sensed input signal based on visualization or optical imaging information can serve as a "predictive" selection of therapeutic energy delivery waveform, therapy, or therapy parameter, which can optionally further be combined with one or more other feedback or other sensed information, such as based upon a tissue impedance, energy delivery phase angle, or other characteristic that can be monitored during the tissue modification or other therapy delivery and used as a feedback signal for signal-processing and controlling adjusting or timing or altering therapy delivery.

Additionally or alternatively, the waveform or other therapy parameter or characteristic or therapy can be selected at least in part based on information derived from the visualization or optical imaging other than information specific to the target site to be treated. For example, if the target tissue to be treated is close to an organ-at-risk (OAR) or a thermally-sensitive area (e.g., such as the colon), the waveform or other therapy parameter or characteristic or therapy can be selected or adjusted based at least in part on such information, such as to help create the smallest possible thermal margin, or to be within a thermal budget specific to such situation. The presence or proximity of such an organ-at-risk or other thermally sensitive area can be determined using the visualization or optical imaging information, such as can use one or more image processing techniques (e.g., segmentation, atlas, trained statistical learning model), and the internal imaging information from a first sensor can be combined with external video or still camera information from a second sensor, such as to provide an indication of patient position, orientation, or movement, that can be image-processed such as for use to help determine the proximity to one or more such other anatomical regions of interest for therapy delivery or therapy avoidance. The visualization or optical imaging information can additionally or alternatively be used to detect one or more structures that should not be modified by therapy, such as to automatically cease applying therapy energy (or provide a user alert) before reaching a thermal margin or limit range of one or more such structure not to be altered by the therapeutic energy delivery. Where the therapeutic energy delivery is affected by one or more other components in the system 100 (e.g., electrical therapy delivered using a forceps to squeeze a vessel closed during sealing), one or more control or other parameters (e.g., grasping force) associated with such other components can be at least one of specified, adjusted, alerted (e.g., using audible, haptic, or visual feedback to a user), limited, or controlled (e.g., using robotic forceps controller circuitry) based at least in part on such visualization or optical imaging information.

For example, different tissues perform differently under compression, such as by a forceps during vessel sealing. In some examples, vessels have no additional benefit to thermal margin or burst pressure from being compressed to a lateral dimension that is less than 40% of its static dimension when uncompressed, while other tissues require greater amounts of compression to reduce the thermal margin.

Furthermore, the vessel sealing or other electrotherapy waveform can also be selected according to other considerations derived from the understanding of the visualization or optical image. Some areas, such as tissue close to another organ, e.g., the colon, can benefit from treatment using as small a thermal margin as possible during the activation and sealing process. But thermal margin can be a trade-off against speed of activation. Slower activation speeds can be used to reduce or minimize thermal margin, such as by only supplying small amounts of energy, before the steam condensation period of the cycle is undertaken. Such therapy timing, rate, and energy considerations can also be controlled such as can be based at least in part on the visualization or optical imaging information.

There are many different tissue materials that a user may wish to activate upon and cut. Such tissues can include fat, mesentery, ligaments, or the like. Such tissues can be activated upon using a different therapy output scheme than what is used for vessel sealing. Such various therapy output schemes can similarly be selected, established, or adapted based at least in part on the visualization or optical imaging information, such as using imaging processing and a trained machine-learning or trained statistical model to identify a tissue type or characteristic of a therapeutic target or non-target before or during therapy administration, including in combination with one or more other factors, such as an electrical characteristic of the tissue or therapy delivery (e.g., tissue impedance or therapy power phase angle).

Thus, the present techniques are not just limited to use in vessel sealing devices, but can be applied elsewhere, including for monopolar and bipolar cutting devices, such as those that are intended to cut tissue hemostatically. For example, the present techniques can be used to visually spot not only vessels on the surface of tissue, but also to use optical imaging techniques (e.g., involving absorption, scattering, or the like) such as to help identify vessels or other structures under the visually-observable surface of such tissues.

For instance, while a surgeon or other user is cutting across a variable section of tissue material having not only different fat levels, but also with vascularity or differences in vascularity, an appropriately tailored therapy setting can be selected before tissue treatment is initiated. This can advantageously help the during-treatment response (either by the user, or by automatic therapy system control using during-treatment feedback signals, e.g., such as tissue impedance, power-delivery phase angle, etc.) to be quicker than it otherwise might be in reacting to a particular situation, for example, such as a large bleed.

Furthermore, the present techniques can be employed to detect a structure that should not be modified or affected by therapy, and to help stop applying energy, for example, as the device is brought into thermal margin distance proximity from the structure to be guarded against being affected or overly affected by the therapy. For example, the ureters can be damaged during gynecological procedures, such as involving electrical or other energy application to nearby tissue. The present techniques, however, can include modifying the output energy with the visualization or optical imaging information indicates that the structure to be guarded is nearby, such as to turn off energy delivery, alert the user, or to request user-confirmation to override such system control.

Thus, the present techniques can include "predictive" or a priori selection of energy delivery (e.g., such as selecting or tailoring an algorithm or a more simplistic waveform) can be combined with one or more feedback signals used during the tissue modification (e.g., such as tissue resistance, tissue reactance, tissue impedance, phase angle, or the like. The present techniques can be employed with electrical energy therapy, monopolar, bipolar, RF, ultrasound, laser, microwave, resistive, among others.

The present system can include or be coupled to an endoscope or other visualization device, such as can provide illumination to a patient-internal tissue site, a photodetector or multi-pixel imaging array such as to transduce response light from the patient internal tissue site for optical imaging. The system can further include electrical signal processing circuitry. This can include imaging processing circuitry, such as which can be used to process the transduced signals into an electrical representation of the optical image. The represented image can be used by the signal-processing circuitry, such as for training of (or use with a trained) neural network or other machine-learning or statistical learning model, such as those described herein. In such a manner, image recognition techniques can be used to help identify a tissue type, tissue material, tissue characteristic, or tissue structure. Such visualization or optical imaging information, in turn, can be used for tailoring one or more parameters of therapy delivery, such as to better treat a region of interest, or to help avoid affecting one or more other sensitive nearby regions or structures. Such a priori visualization or optical imaging information can be used in combination with ongoing information obtained during therapy delivery, such as about a tissue characteristic or a therapy characteristic, to further adjust, limit, or control therapy delivery. Also, examples herein can include providing a user of the end effector assembly 104 with the capability of receiving visual, tactile or audible feedback from the processing unit 122 such as to help indicate or suggest to the operator cease or shorten an energy application period based upon the amount of tissue pressure or closure force, e.g., such as after energy application and an appropriate tissue pressure or closure force, or to inform the user that too great of tissue pressure or closure force is being applied, such as in view of a particular sensed tissue type or tissue parameter being observed within or being grasped by the end effector.

The processing unit 122 can include or use processing circuitry. The processing unit 122 is not limited to a single unit or circuit. The processing unit 122 can include multiple sources of processing, and some may be physically separate or remotely located from the device. In an example, the processing unit 122 can include or use memory circuitry comprising instructions that, when executed by the processing circuitry of the processing unit 122, can cause the processing unit 122 to perform an inspection operation using the sensor 114. The processing circuitry can include or use image-processing circuitry configured such as to determine a contact area of the tissue compressed between the first jaw member 108 and the second jaw member 110 using the tissue image and a trained machine learning model. The processing circuitry can include or use image-processing circuitry configured to determine a contact area of the tissue compressed between the first jaw member 108 and the second jaw member 110 using the tissue image and an automated algorithm. The processing circuitry can include or use image-processing circuitry configured to determine a cross-sectional diameter of at least one vessel contained in the tissue compressed between the first jaw member 108 and the second jaw member 110 using the tissue image and a trained machine learning model. The processing circuitry can include or use image-processing circuitry configured to determine a cross-sectional diameter of at least one vessel contained in the tissue compressed between the first jaw member 108 and the second jaw member 110 using the tissue image and an automated algorithm.

Figure 2:
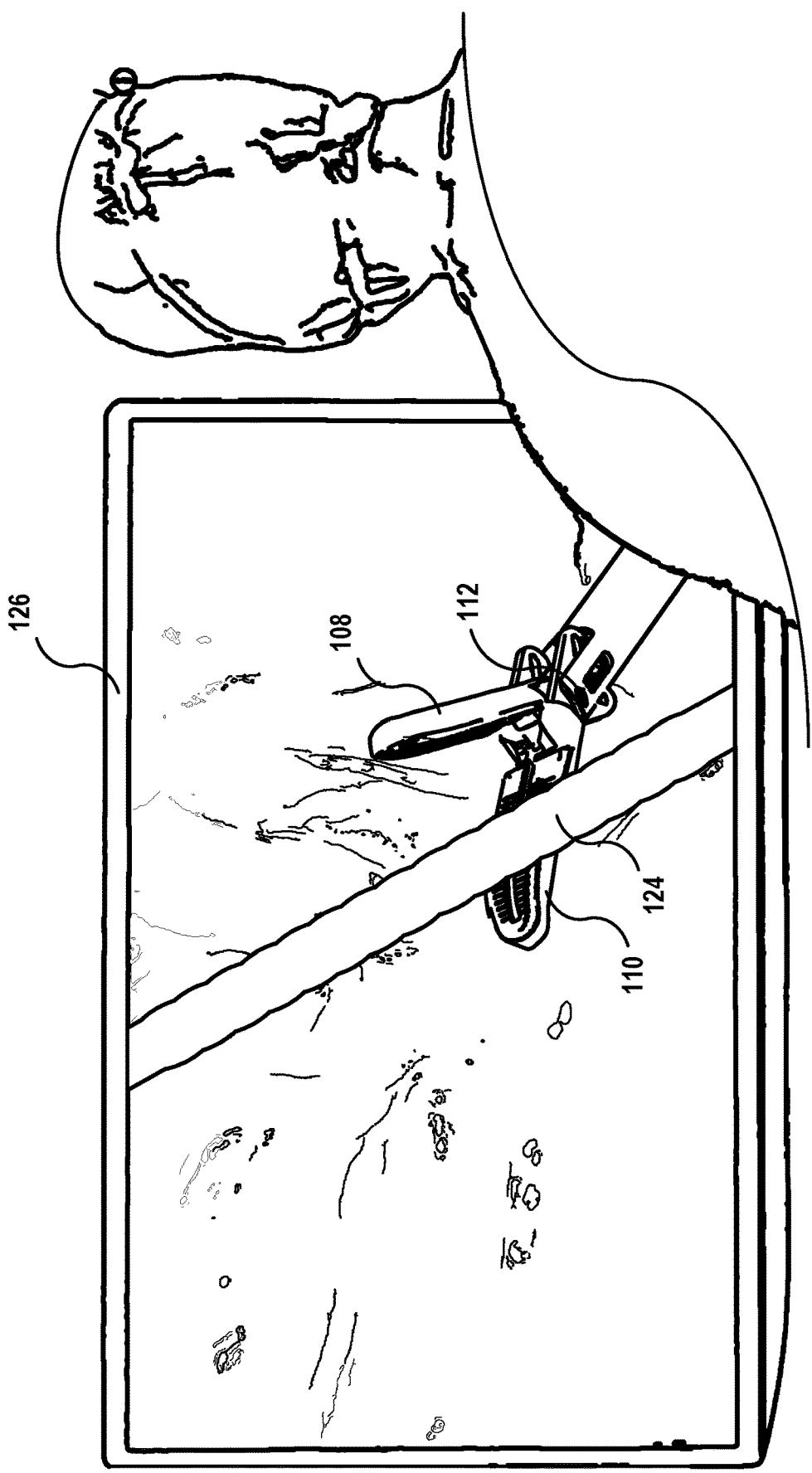
FIG. 2 illustrates an example of an electrosurgical system in use by a surgeon.

FIG. 2 illustrates an example of an electrosurgical system in use by a surgeon. The system can include or use the one or more sensors 114 configured to inspect tissue compressed between the first jaw member 108 and the second jaw member 110. The sensor 114 can also inspect tissue in any location in view of the sensor; adjacent the end effector assembly 104; or located between the first jaw member 108 and the second jaw member 110, before or after the tissue is compressed by the end effector assembly 104 or without eventual compression thereby. For example, the tissue image can be a precompression image used by the processing unit 122 to help determine a target clamping force of the jaw assembly. Also, the tissue image can be an image of compressed tissue between the first jaw member 108 and the second jaw member 110 and can be used by the processing unit 122 to help determine, modulate, or adjust a parameter of the jaw assembly such as the target clamping force applied to the compressed tissue.

Also, mechanical or electrical properties of the tissue can be measured by the one or more sensors 114 such as to help establish, adjust, or modulate a parameter of the jaw assembly. In an example, the electrosurgical system can include or use spectroscopy or ionizing circuitry that can be used such as to help determine a composition of the tissue. Optical sensing circuitry can also be used such as at one or more IR wavelengths or with dyes or fluorescence to help visualize the tissue to the sensor 114.

As previously described, the sensor 114 can be a camera capable of capturing a tissue image, and the tissue image can include device-recognizable features of the tissue. For example, the camera can a provide real time, inline, or otherwise concurrent video monitoring feed for the surgeon and can use frames of the feed to capture the device-recognizable features of the tissue. The video monitoring feed can be viewed on a display 126 during a procedure. The video monitoring feed can include or use one or more visual or tactile or audible indicators such as to provide feedback to the surgeon during the procedure. The indicators can provide feedback to the surgeon such as to help the surgeon manually apply the target clamping force using the end effector assembly 104. Additionally or alternatively, the device-recognizable features can be used by the processing unit 122 to help automatically apply the target clamping force using the end effector assembly 104.

In an example, data from the sensor 114 can be used by seal assessment circuitry such as to ensure a desired seal of tissue after treatment. For example the data from the sensor 114, such as oximeter data or vessel color data, can be used such as to indicate a presence of hemoglobin in the tissue. In an example, the seal assessment circuitry can include or use a processor for automatically reviewing one or more characteristics corresponding to a desired seal, the characteristics being determined from the data. For example, a surgeon or operator can be alerted by the system if the characteristics can be determined when desired tissue characteristics are not detected following a treatment session. Also, if one or more undesired tissue characteristics are detected, a surgeon or operator can be alerted by the system following the treatment session.

Figure 3:
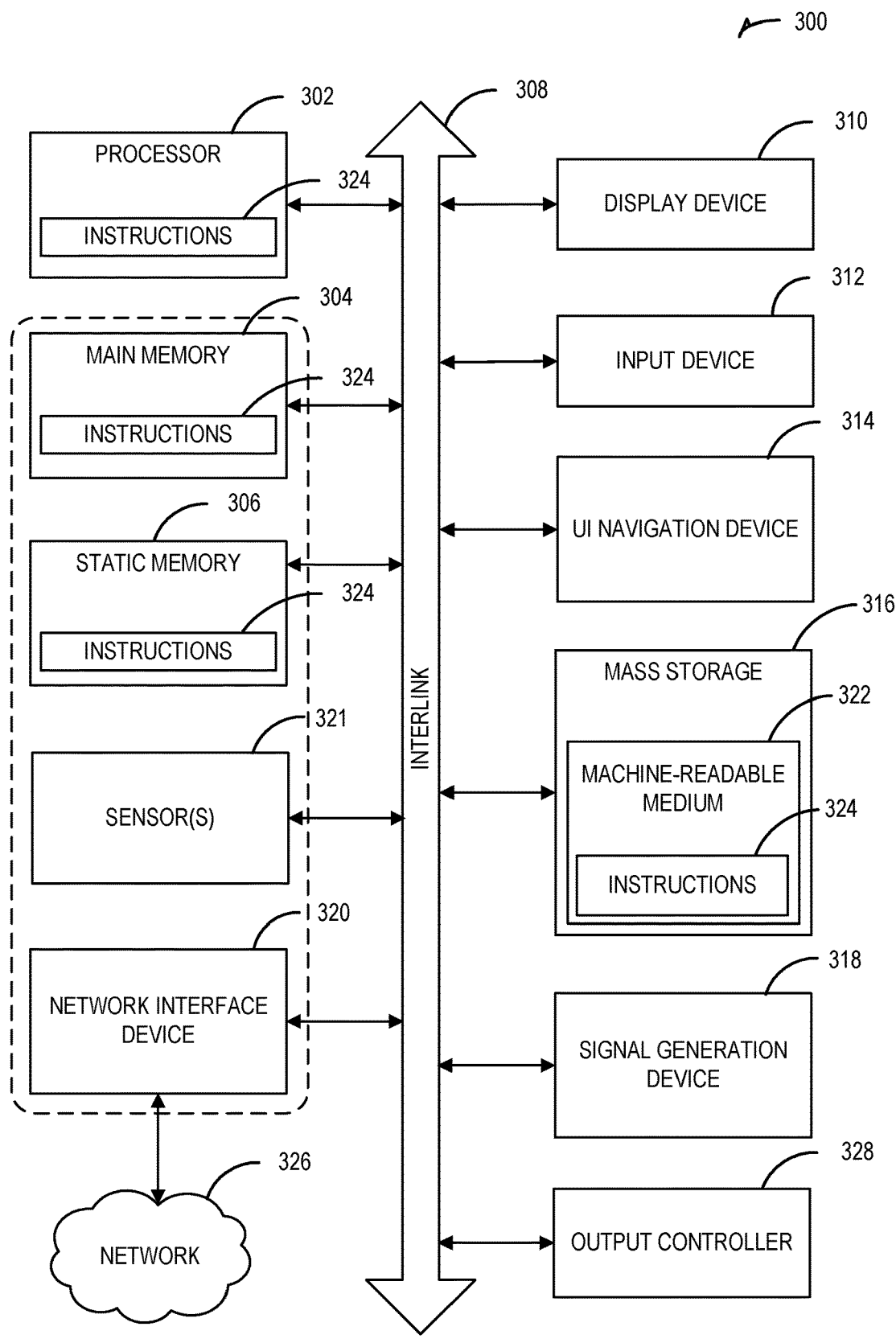
FIG. 3 shows a block diagram of an example of a machine on which one or more of the methods as discussed herein can be implemented.

FIG. 3 shows a block diagram of an example of a machine 300 on which one or more of the methods as discussed herein can be implemented. In one or more examples, one electrosurgical system 100 can be implemented by the machine 300. In alternative examples, the machine 300 operates as a standalone device or may be connected (e.g., networked) to other machines. In one or more examples, the electrosurgical system 100 can include one or more of the items of the machine 300. In a networked deployment, the machine 300 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 300 includes processor 302 (e.g., a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 321 (e.g., a transducer that converts one form of energy (e.g., light, heat, electrical, mechanical, or other energy) to another form of energy), or the like, or a combination thereof), a main memory 304 and a static memory 306, which communicate with each other via a bus 308. The machine 300 (e.g., computer system) may further include a video display unit 310 (e.g., a liquid crystal display (LCD) or a cathode ray tube (CRT)). The machine 300 also includes an alphanumeric input device 312 (e.g., a keyboard), a user interface (UI) navigation device 314 (e.g., a mouse), a disk drive or mass storage unit 316, a signal generation device 318 (e.g., a speaker), and a network interface device 320.

The disk drive or mass storage unit 316 includes a machine-readable medium 322 on which is stored one or more sets of instructions and data structures (e.g., software) 324 embodying or used by any one or more of the methodologies or functions described herein. The instructions 324 may also reside, completely or at least partially, within the main memory 304 or within the processor 302 during execution thereof by the machine 300, the main memory 304 and the processor 302 also constituting machine-readable media.

The machine 300 as illustrated includes an output controller 328. The output controller 328 manages data flow to/from the machine 300. The output controller 328 is sometimes called a device controller, with software that directly interacts with the output controller 328 being called a device driver.

While the machine-readable medium 322 is shown in an example to be a single medium, the term "machine-readable medium" may include a single medium or multiple media (e.g., a centralized or distributed database, or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 324 may further be transmitted or received over a communications network 326 using a transmission medium. The instructions 324 may be transmitted using the network interface device 320 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Figure 4:
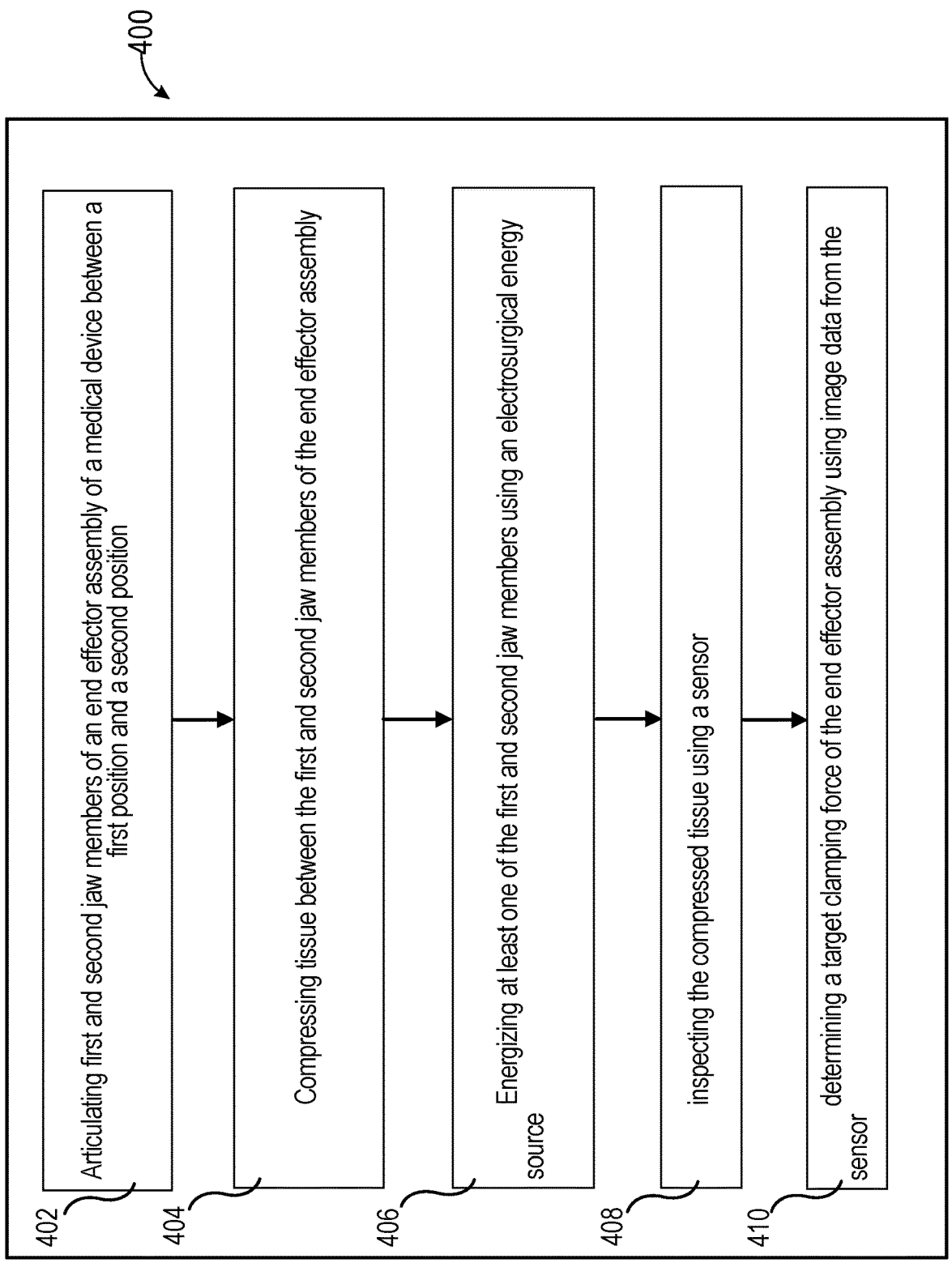
FIG. 4 is a flowchart of a method of using an example of an electrosurgical system including a jawed electrosurgical device.

FIG. 4 is a flowchart of a method of using an example of an electrosurgical system including a jawed electrosurgical device. In an example, a method of treating tissue 400 can be performed using one of several electrosurgical systems described herein. At 402, first and second jaw members of an end effector assembly of a medical device can be articulated between a first position and a second position. At 404, tissue can be compressed between the first and second jaw members of the end effector assembly. At 406, at least one of the first and second jaw members can be energized using an electrosurgical energy source. At 408, compressed tissue can be inspected using the using a sensor. And, at 410, a target clamping force of the end effector assembly can be determined using image data from the sensor.

Figure 5:
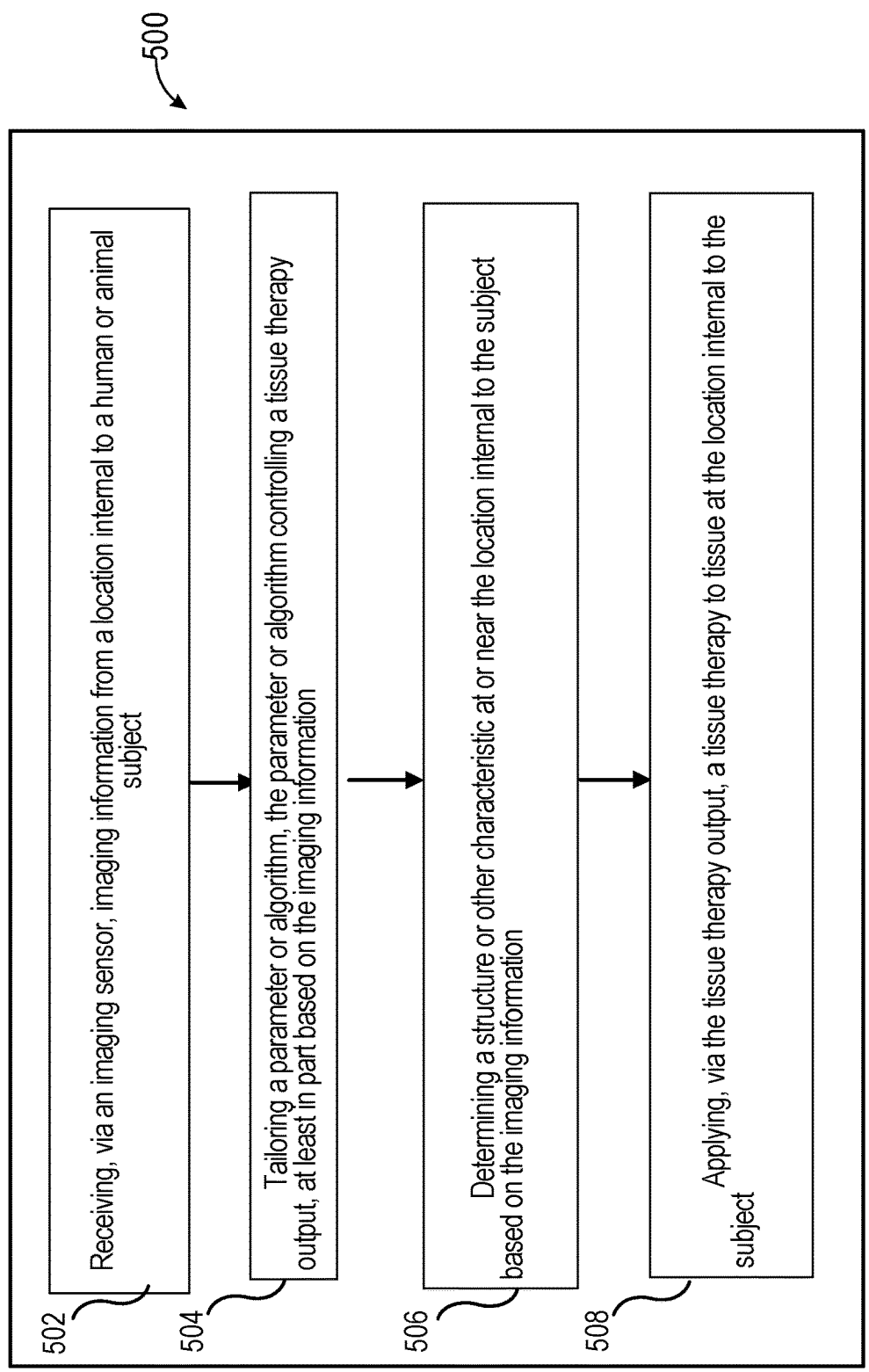
FIG. 5 is a flowchart of a method of using an example of a general electrosurgical system.

FIG. 5 is a flowchart of a method of using an example of a general electrosurgical system. In an example, a method of treating tissue 500 can be performed using one of several electrosurgical systems such as described herein. At 502, imaging information can be received, such as via an imaging sensor, from a location internal to a human or animal subject. Imaging information can also be received from a location external to a human or animal subject. At 504, structure or other characteristic at or near the location internal or external to the subject can be determined based on the imaging information. And, at 506, a parameter or algorithm, such as for controlling the tissue therapy output, can be tailored at least in part based on the imaging information. And, at 508, a tissue therapy can be applied, such as via a tissue therapy output, to tissue at the location internal or external to the subject. For example, tailoring a parameter or algorithm can include tailoring a target clamping force of a jaw assembly of an end effector, based at least in part on the imaging information, such as for sealing, cautery, or cutting. Also, tailoring a parameter or algorithm can include tailoring an energy waveform based at least in part on the imaging information such as for sealing, cautery, or cutting. For example, tailoring a parameter or algorithm can include or use tailoring an electrosurgical energy signal based at least in part on the imaging information. In some examples, tailoring an energy waveform can include tailoring an energy waveform for any type of energy-based tissue treatment, also including devices for ablating, dessicating, sectioning or fulgrating. Tailoring an energy waveform is not limited to forceps type devices having jaws or bipolar capabilities. For example, tailoring an energy waveform based on imaging information can be applied to any electrosurgical device, including any other bipolar or monopolar devices, such as but not limited to, a spatula, a bovie, a scalpel, and the like.

The systems described herein can tailor output delivered to a treatment device based on one or more received inputs from one or more sensors (e.g., image information from an image sensor, force information from a force sensor, electrical information from an electrical sensor), and can tailor one or more of: an energy-related output and a force-related output. In the illustrative example provided, the energy output is shown as a radiofrequency energy delivered to an electrode of a forceps, but can also include ultrasonic, microwave, electromagnetic, resistive, thermal, laser energy in a forceps or in other types of treatment devices. In the illustrative example, the force can be applied mechanisms including compression, displacement, pressure, such as those that occur with the closure of jaws in a forceps by movement of the user in a hand-operated device, or by way of a drive in a robotic device.

NOTES AND EXAMPLES

The following, non-limiting examples, detail certain aspects of the present subject matter to solve the challenges and provide the benefits discussed herein, among others.

Aspect 1 is a system for imaging and treating tissue, the system comprising: an imaging sensor, adapted to receive imaging information from a location internal to a human or animal subject; a tissue therapy output for applying a tissue therapy to tissue at the location internal to the subject; and controller circuitry, comprising signal-processing circuitry configured for image-processing the imaging information to determine a structure or other characteristic at or near the location internal to the subject, and to tailor a parameter or algorithm, controlling the tissue therapy output, at least in part based on the imaging information.

In Aspect 2, the subject matter of Aspect 1, wherein the imaging sensor includes a camera.

In Aspect 3, the subject matter of Aspect 2, wherein the controller circuitry is configured to generate a tissue image of the tissue at the location internal to the subject.

In Aspect 4, the subject matter of any of Aspects 1-3, including an end effector including the tissue therapy output.

In Aspect 5, the subject matter of Aspect 4, wherein the end effector includes a forceps comprising a jaw assembly including: a first jaw member; and a second jaw member pivotably coupled to the first jaw member, wherein: the jaw fassembly is movable between a first position, in which the first and second jaw members are spaced apart from each other, and a second position, in which the first and second jaw members are positioned closer to each other than in the first position; and at least one of the first and second jaw members includes the tissue therapy output.

In Aspect 6, the subject matter of Aspect 5, wherein: the parameter includes a target clamping force of the jaw assembly; and the controller circuitry is configured to establish or adjust the target clamping force using the imaging information.

In Aspect 7, the subject matter of any of Aspects 5-6, wherein the controller circuitry is configured to provide at least one of a control signal to the end effector assembly or a user alert to a user controlling the end effector assembly, based at least in part on the imaging information.

In Aspect 8, the subject matter of any of Aspects 5-7, wherein the controller circuitry is configured to: recognize one or more features from a tissue image of the tissue compressed between the first jaw member and the second jaw member; and the recognized one or more features of the tissue comprise a width of tissue compressed between the first jaw member and the second jaw member, the width of tissue being a measurement of tissue contacting the jaw members between respective proximal portions and respective distal portions of the jaw members.

In Aspect 9, the subject matter of any of Aspects 5-8, wherein the controller circuitry is configured to: recognize one or more features from a tissue image of the tissue compressed between the first jaw member and the second jaw member; and the recognized one or more features of the tissue comprise an indication of an amount of tissue compressed between the first jaw member and the second jaw member.

In Aspect 10, the subject matter of any of Aspects 5-9, wherein the controller circuitry is configured to: recognize one or more features from a tissue image of the tissue compressed between the first jaw member and the second jaw member; and the recognized one or more features of the tissue comprise an indication of an approximate diameter of a vessel compressed between the first jaw member and the second jaw member.

In Aspect 11, the subject matter of any of Aspects 5-10, wherein the controller circuitry includes image-processing circuitry configured to determine a contact area of the tissue compressed between the first jaw member and the second jaw member using the tissue image.

In Aspect 12, the subject matter of any of Aspects 1-11, wherein: the parameter includes an energy characteristic of the tissue therapy; and the controller circuitry is configured to modulate the energy characteristic of the tissue therapy using the imaging information.

In Aspect 13, the subject matter of any of Aspects 1-12, wherein the controller circuitry is configured to modulate the parameter including modulating an electrosurgical energy signal at least in part based on the imaging information including imaging information from a therapy target structure location.

In Aspect 14, the subject matter of any of Aspects 1-13, wherein the controller circuitry is configured to: recognize one or more features from the imaging information including a tissue image of the tissue at the location internal to the subject; and establish or adjust an electrosurgical energy signal supplied by the tissue therapy output based at least in part on the recognized one or more features from the imaging information including the tissue image of the tissue.

Aspect 15 is a system for treating tissue, the system comprising: an imaging sensor, adapted to receive imaging information from a location internal to a human or animal subject; a tissue therapy output for applying tissue therapy to tissue at the location internal to the subject; and controller circuitry, comprising signal-processing circuitry configured for image-processing the imaging information to determine a structure or other characteristic at or near the location internal to the subject, and to tailor a tissue therapy compression force parameter, controlling the tissue therapy output, at least in part based on the imaging information.

In Aspect 16, the subject matter of Aspect 15, wherein the imaging sensor includes a camera.

In Aspect 17, the subject matter of any of Aspects 15-16, including an end effector including a jaw assembly, wherein the compression force parameter includes a target clamping force of the jaw assembly.

Aspect 18 is a method for treating tissue comprising: receiving, via an imaging sensor, imaging information from a location internal to a human or animal subject; determining a structure or other characteristic at or near the location internal to the subject based on the imaging information; tailoring a parameter or algorithm, the parameter or algorithm controlling a tissue therapy output, at least in part based on the imaging information; and applying, via the tissue therapy output, a tissue therapy to tissue at the location internal to the subject.

In Aspect 19, the subject matter of Aspect 18, wherein the imaging sensor includes a camera.

In Aspect 20, the subject matter of any of Aspects 18-19, wherein the tailoring a parameter or algorithm includes tailoring a target clamping force of a jaw assembly of an end effector, based at least in part on the imaging information, for at least one of sealing, cautery, or cutting.

In Aspect 21, the subject matter of any of Aspects 18-20, wherein tailoring a parameter or algorithm includes tailoring an electrosurgical energy signal based at least in part on the imaging information.

Aspect 22 is a system comprising: visualization or optical imaging componentry, adapted to receive visualization or optical imaging information from a location internal to a human or animal subject; a tissue therapy output for applying energy to tissue at a location internal to the subject; and controller circuitry, comprising signal-processing circuitry configured for image-processing the visualization or optical imaging information for training or using a trained model for image recognition to determine a structure or other characteristic at or near the location internal to the subject, and to tailor a parameter or algorithm, controlling the tissue therapy output, at least in part based on the visualization or optical imaging information.

In Aspect 23, the subject matter of Aspect 22, further comprising an electrical tissue characteristic sensor arranged to sense an electrical characteristic of tissue located at or near the location internal to the subject, and wherein the controller circuitry is configured for controlling the tissue therapy output at least in part based on information about the sensed electrical characteristic.

In Aspect 24, the subject matter of any of Aspects 22-23, wherein the tissue therapy output further includes a mechanical device for assisting in applying the energy to the tissue at the location internal to the subject, and wherein the controller circuitry is further configured to provide at least one of a control signal to the mechanical device or a user alert to a user controlling the mechanical device, based at least in part on the visualization or optical imaging information.

In Aspect 25, the subject matter of any of Aspects 22-24, wherein the controller circuitry is configured for controlling the tissue therapy output at least in part based on visualization or optical imaging information from a therapy target structure location.

In Aspect 26, the subject matter of any of Aspects 22-25, wherein the controller circuitry is configured for controlling the tissue therapy output based at least in part on visualization or optical imaging information from a therapy avoidance structure location.

Aspect 27 is a method of using the system of Aspect 22 to control therapy delivery or provide a user alert.

Aspect 28 is a device-readable medium including instructions to perform the method of Aspect 27.

Aspect 29 is a device-readable medium including a trained neural network, machine-learning, or other model to perform the method of Aspect 27, wherein the model uses the visualization or optical imaging information.

Aspect 30 is a system for treating tissue comprising: an end effector assembly of a medical device, the end effector assembly comprising a jaw assembly including: a first jaw member; and a second jaw member pivotably coupled to the first jaw member wherein: the jaw assembly is movable between a first position wherein the first and second jaw members are spaced apart from each other and a second position wherein the first and second jaw members are positioned closer to each other; and at least one of the first and second jaw members are adapted to connect to an electrosurgical energy source; a sensor configured to inspect tissue; and a processing unit configured to receive data from the sensor and modulate a parameter of the jaw assembly using the data.

In Aspect 31, the subject matter of Aspect 30, wherein the parameter of the jaw assembly is a target clamping force.

In Aspect 32, the subject matter of any of Aspects 30-31, wherein the parameter of the jaw assembly is a frequency or current of energy electrosurgical energy from the electrosurgical energy source.

In Aspect 33, the subject matter of any of Aspects 30-32, wherein the tissue is compressed between the first jaw member and the second jaw member for inspection therein.

In Aspect 34, the subject matter of any of Aspects 30-33, wherein the sensor is a camera.

In Aspect 35, the subject matter of Aspect 34, wherein the processing unit is configured to generate a tissue image of the tissue compressed between the first jaw member and the second jaw member, the tissue image including device-recognizable features of the tissue.

In Aspect 36, the subject matter of Aspect 35, wherein the device-recognizable features of the tissue comprise an amount of tissue compressed between the first jaw member and the second jaw member.

In Aspect 37, the subject matter of any of Aspects 35-36, wherein the device-recognizable features of the tissue comprise a width of tissue compressed between the first jaw member and the second jaw member, the width of tissue being a measurement of tissue contacting the jaw members between a respective proximal ends and respective distal ends of the jaw members.

In Aspect 38, the subject matter of any of Aspects 35-37, wherein the device-recognizable features of the tissue comprise an approximated diameter of a vessel compressed between the first jaw member and the second jaw member.

In Aspect 39, the subject matter of any of Aspects 35-38, wherein the processing unit includes memory circuitry comprising instructions that, when executed by at least one processor circuit, cause the processing unit to perform an inspection operation using the sensor.

In Aspect 40, the subject matter of Aspect 39, wherein the at least one processor circuit comprises image-processing circuitry configured to determine a contact area of the tissue compressed between the first jaw member and the second jaw member using the tissue image and a trained machine learning model.

In Aspect 41, the subject matter of any of Aspects 39-40, wherein the at least one processor circuit comprises image-processing circuitry configured to determine a contact area of the tissue compressed between the first jaw member and the second jaw member using the tissue image and an automated algorithm.

In Aspect 42, the subject matter of any of Aspects 39-41, wherein the at least one processor circuit comprises image-processing circuitry configured to determine a cross-sectional diameter of at least one vessel contained in the tissue compressed between the first jaw member using the tissue image and a trained machine learning model.

In Aspect 43, the subject matter of any of Aspects 39-42, wherein the at least one processor circuit comprises image-processing circuitry configured to determine a cross-sectional diameter of at least one vessel contained in the tissue compressed between the first jaw member using the tissue image and an automated algorithm.

Aspect 44 is a system for treating tissue comprising: an end effector assembly of a medical device, the end effector assembly comprising a jaw assembly including: a first jaw member; and a second jaw member pivotably coupled to the first jaw member wherein: the jaw assembly is movable between a first position wherein the first and second jaw members are spaced apart from each other and a second position wherein the first and second jaw members are positioned closer to each other; and at least one of the first and second jaw members are adapted to connect to an electrosurgical energy source; a sensor configured to inspect tissue compressed between the first jaw member and the second jaw member; and a processing unit configured to receive image data from the sensor and determine a target clamping force of the jaw assembly using the data.

Aspect 45 is a method for treating tissue comprising: articulating an end effector assembly of a medical device between: a first position wherein first and second jaw members of the assembly are spaced apart from each other; and a second position wherein the first and second jaw members are positioned closer to each other; compressing the tissue between the first and second jaw members of the end effector assembly; energizing at least one of the first and second jaw members using an electrosurgical energy source; inspecting the compressed tissue using a sensor; and determining a target clamping force of the end effector assembly using image data from the sensor.

In Aspect 46, the subject matter of Aspect 45, wherein the sensor is a camera.

In Aspect 47, the subject matter of Aspect 46, wherein determining a target clamping force of the end effector assembly using image data from the sensor includes generating a tissue image including device-recognizable features of the tissue.

In Aspect 48, the subject matter of Aspect 47, wherein the device-recognizable features of the tissue comprise an amount of tissue compressed between the first jaw member and the second jaw member.

In Aspect 49, the subject matter of Aspect 48, wherein the device-recognizable features of the tissue comprise a width of tissue compressed between the first jaw member and the second jaw member, the width of tissue being a measurement of tissue contacting the jaw members between a respective proximal ends and respective distal ends of the jaw members.

Aspect 50 is at least one machine-readable medium including instructions that, when executed by processing circuitry, cause the processing circuitry to perform operations to implement of any of Aspects 1-49.

Aspect 51 is an apparatus comprising means to implement of any of Aspects 1-49.

Aspect 52 is a system to implement of any of Aspects 1-49.

Aspect 53 is a method to implement of any of Aspects 1-49.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for imaging and treating tissue, the system comprising:
an imaging sensor, adapted to receive imaging information from a location internal to a human or animal subject;
an end effector including an electrical tissue therapy output for applying a tissue therapy to tissue at the location internal to the human or animal subject to electrically coagulate, cauterize or cut the tissue, wherein the end effector comprises a jaw assembly comprising:
a first jaw member; and
a second jaw member pivotably coupled to the first jaw member, wherein:
the jaw assembly is movable between a first position, in which the first and second jaw members are spaced apart from each other, and a second position, in which the first and second jaw members are positioned closer to each other than in the first position;
wherein at least one of the first and second jaw members includes the electrical tissue therapy output; and controller circuitry, comprising signal-processing circuitry configured for image-processing the imaging information to determine a type of tissue at or near the location internal to the human or animal subject, and to tailor a parameter or algorithm, controlling the electrical tissue therapy output, at least in part based on the imaging information.

2. The system of claim 1, wherein:
the imaging sensor includes a video camera sensor capable of capturing tissue images having an array of pixels of the tissue; and
the controller circuitry is configured to generate a tissue image of the tissue at the location internal to the human or animal subject and to recognize a structure of characteristic of the tissue, including the tissue type, based on pixel analysis.

3. The system of claim 2, wherein the controller circuitry is configured to:
recognize one or more features from pixels of a tissue image of the tissue compressed between the first jaw member and the second jaw member; and
the recognized one or more features of the tissue comprise a width or diameter of tissue compressed between the first jaw member and the second jaw member.

4. The system of claim 3, wherein the controller circuitry includes image-processing circuitry configured to determine a contact area of the tissue compressed between the first jaw member and the second jaw member using the imaging information.

5. The system of claim 2, wherein the controller circuitry is configured to:
recognize one or more features from pixels of a tissue image of the tissue compressed between the first jaw member and the second jaw member; and
the recognized one or more features of the tissue comprise an indication of an amount of tissue compressed between the first jaw member and the second jaw member.

6. The system of claim 2, wherein the controller circuitry is configured to determine they type of tissue by determining color of pixels in the array of pixels.

7. The system of claim 1, wherein:
the parameter includes a target clamping force of the jaw assembly; and
the controller circuitry is configured to establish or adjust the target clamping force using the imaging information.

8. The system of claim 1, wherein the controller circuitry is configured to provide at least one of a control signal to the jaw assembly or a user alert to a user controlling the jaw assembly, based at least in part on the imaging information.

9. The system of claim 1, wherein:
the parameter includes an energy characteristic of the tissue therapy; and
the controller circuitry is configured to modulate the energy characteristic of the tissue therapy using the imaging information.

10. The system of claim 1, wherein the controller circuitry is configured to modulate the parameter including modulating an electrosurgical energy signal at least in part based on the imaging information including imaging information from a therapy target structure location.

11. The system of claim 1, wherein the controller circuitry is configured to:
recognize one or more features from the imaging information including a tissue image of the tissue at the location internal to the human or animal subject; and
establish or adjust an electrosurgical energy signal supplied by the electrical tissue therapy output based at least in part on the recognized one or more features from the imaging information including the tissue image of the tissue.

12. The system of claim 1, wherein the controller circuitry is configured to determine types of tissue comprising fat, mesentery and ligament.

13. A system for treating an anatomic vessel, the system comprising: an imaging sensor, adapted to receive video imaging information from a location internal to a human or animal subject; an end effector including a jaw assembly configured to apply an adjustable clamping force to the anatomic vessel in the jaw assembly; a tissue therapy output for applying tissue therapy to the anatomic vessel from the jaw assembly at the location internal to the human or animal subject, the tissue therapy output comprising radiofrequency energy; and controller circuitry, comprising signal-processing circuitry configured for image-processing the video imaging information to determine a structure or other characteristic of the anatomic vessel in the jaw assembly, determine a target clamping force for the jaw assembly at least in part based on the determined structure or other characteristic of the anatomic vessel in the jaw assembly; and provide an output signal for operating the jaw assembly to adjust generation of the adjustable clamping force based on the video imaging information from the imaging sensor in combination with adjusting a magnitude of the tissue therapy output to generate sufficient tissue pressure to, along with the tissue therapy output, seal the anatomic vessel.

14. The system of claim 13, further comprising a force sensor connected to the jaw assembly to sense the anatomic vessel in the jaw assembly, wherein the controller circuitry can adjust the tissue therapy output based on output of the force sensor.

15. The system of claim 13, wherein the output signal comprises an alarm for a user to adjust the clamping force or a signal for a motor to adjust the clamping force.

16. The system of claim 13, wherein the controller circuitry is configured to determine a type of tissue at or near the location internal to the human or animal subject and determine a target closure force for the jaw assembly for the type of tissue determined.

17. A system comprising:
visualization or optical imaging componentry, adapted to receive visualization or optical imaging information of tissue from a location internal to a human or animal subject;
a tissue therapy output for applying energy to tissue at a location internal to the human or animal subject, wherein the tissue therapy output comprises electrical energy to electrically coagulate, cauterize or cut the tissue;
controller circuitry, comprising signal-processing circuitry configured for image-processing the visualization or optical imaging information for training or using a trained model for image recognition to determine a type of the tissue, and to tailor a parameter or algorithm, controlling the tissue therapy output, at least in part based on the visualization or optical imaging information; and
an electrical tissue characteristic sensor arranged to sense an electrical characteristic of the tissue, and wherein the controller circuitry is configured for controlling the tissue therapy output at least in part based on information about the sensed electrical characteristic.

18. The system of claim 17, wherein the tissue therapy output further includes a mechanical device for assisting in applying the energy to the tissue at the location internal to the human or animal subject, and wherein the controller circuitry is further configured to provide at least one of a control signal to a drive mechanism for the mechanical device or a user alert to a user controlling the mechanical device, based at least in part on the visualization or optical imaging information.

19. The system of claim 18, wherein the controller circuitry is configured for controlling the tissue therapy output at least in part based on visualization or optical imaging information from a therapy target structure location or a therapy avoidance structure location, wherein the therapy avoidance structure location comprises an organ-at-risk and the controller circuitry is configured to adjust output of the electrical tissue therapy output based on proximity of the mechanical device to the organ-at-risk.

20. The system of claim 19, wherein the therapy avoidance structure location comprises colon tissue or ureter tissue.

* * * * *